United States Patent [19]

Kaali et al.

[11] Patent Number: 4,827,946
[45] Date of Patent: May 9, 1989

[54] ELECTRIFIED VAGINAL RING

[76] Inventors: Steven Kaali, Penthouse E, 225 E. 23rd St., New York, N.Y. 10021; Peter M. Schwolsky, 4101 Cathedral Ave., Washington, D.C. 20016

[21] Appl. No.: 141,132
[22] Filed: Jan. 6, 1988
[51] Int. Cl.⁴ ............................................. A61F 5/46
[52] U.S. Cl. ...................................... 128/830; 128/834
[58] Field of Search ............... 128/127, 784, 788, 130, 128/131, 734

[56] References Cited

U.S. PATENT DOCUMENTS

| | | | |
|---|---|---|---|
| 216,281 | 6/1879 | Looney | 128/127 |
| 520,895 | 6/1894 | Petit | 128/788 |
| 563,387 | 7/1896 | Keller | 128/788 X |
| 635,004 | 10/1899 | Souder | 128/788 X |
| 3,866,613 | 2/1975 | Kenny et al. | 128/127 X |
| 4,396,019 | 8/1983 | Perry Jr. | 128/778 X |
| 4,616,640 | 10/1986 | Kaali et al. | 128/130 |
| 4,669,478 | 6/1987 | Robertson | 128/630 |

Primary Examiner—Robert A. Hafer
Assistant Examiner—Kevin G. Rooney
Attorney, Agent, or Firm—Charles W. Helzer

[57] ABSTRACT

An electrified vaginal ring comprising an annular ring member fabricated of a medical grade polymer, elastomer, silicone or other comparable plastic material which is compatible with human tissue and fluids and physically proportioned to fit within the vagina of a female human being or other mammal while surrounding the cervix. The annular ring member has at least two physically spaced-apart, electrically conductive surfaces preferably in the form of spaced-apart bands of conductive material extending around either the periphery of the central opening through the annular ring member, or around the outside perimeter of the annular ring member. The electrically conductive surfaces may be comprised of platinum, a platinum alloy, or other comparable electrically conductive material that is electro-deposited, sprayed or otherwise secured to the annular ring member with the conductive material also being compatible with human tissue and fluids. At least one miniaturized electric cell or a plurality of such cells interconnected to form a miniaturized battery is molded within the body of the annular ring member with respective one of its opposite polarity terminals electrically connected to respective ones of the spaced-apart electrically conductive surfaces.

12 Claims, 5 Drawing Sheets

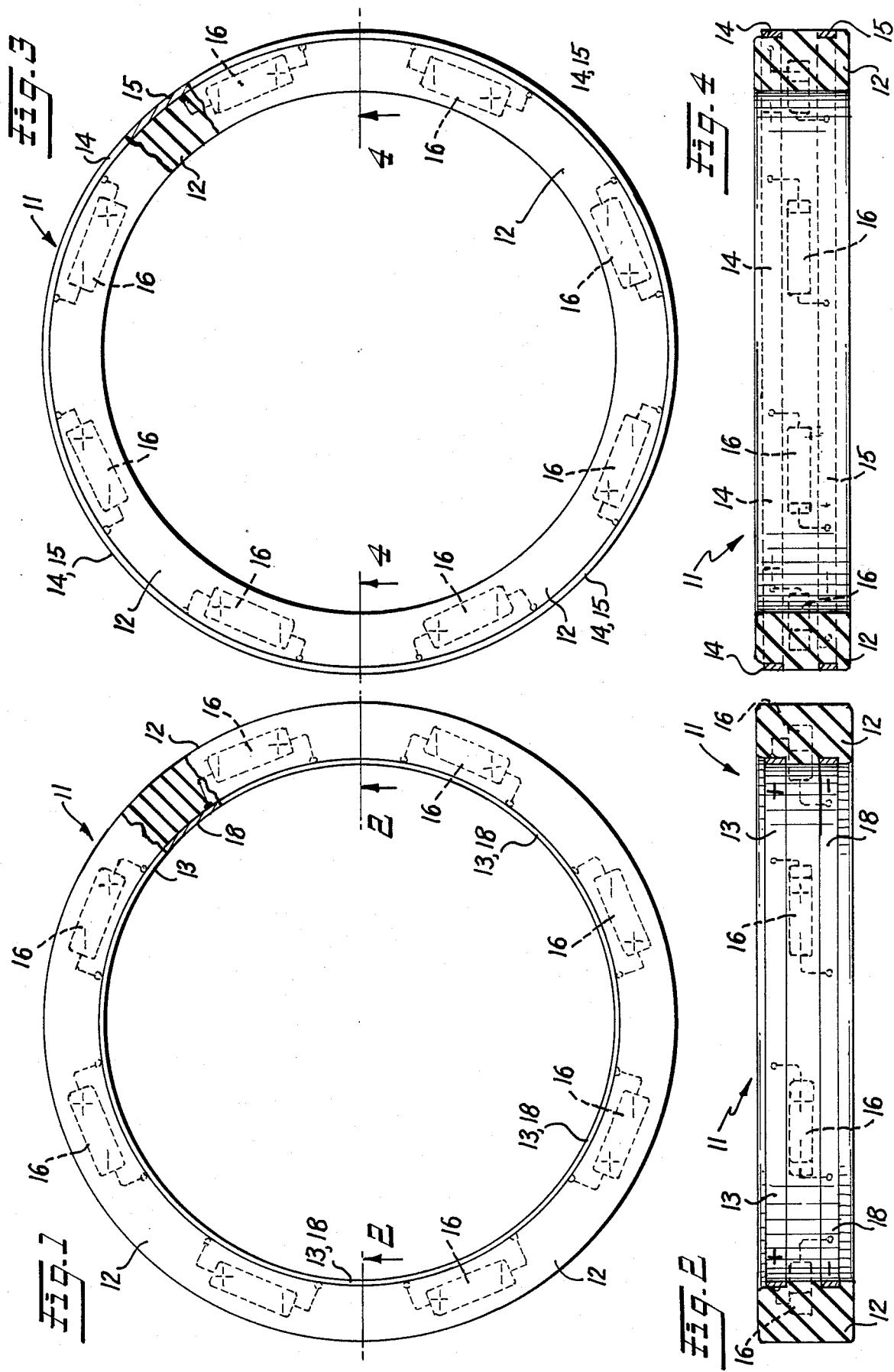

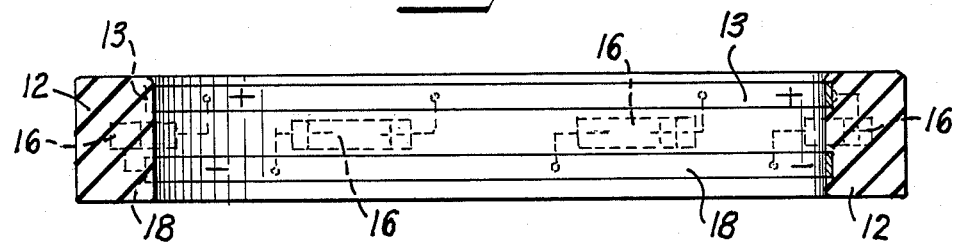
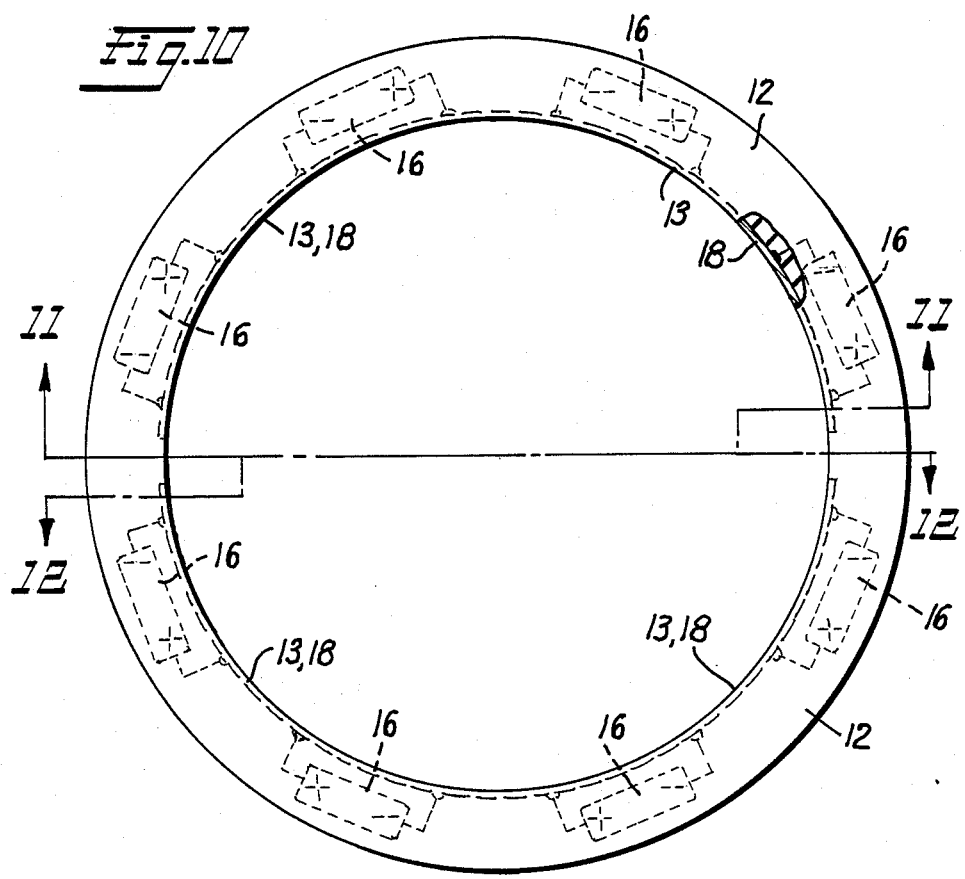
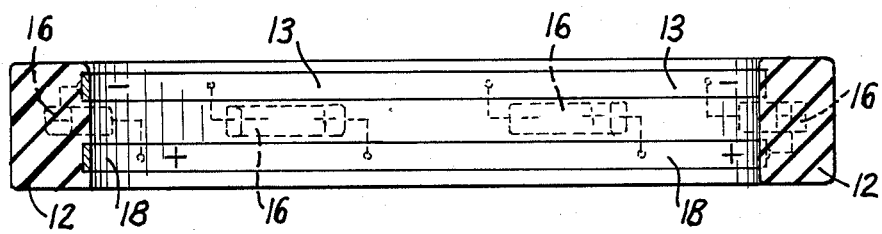

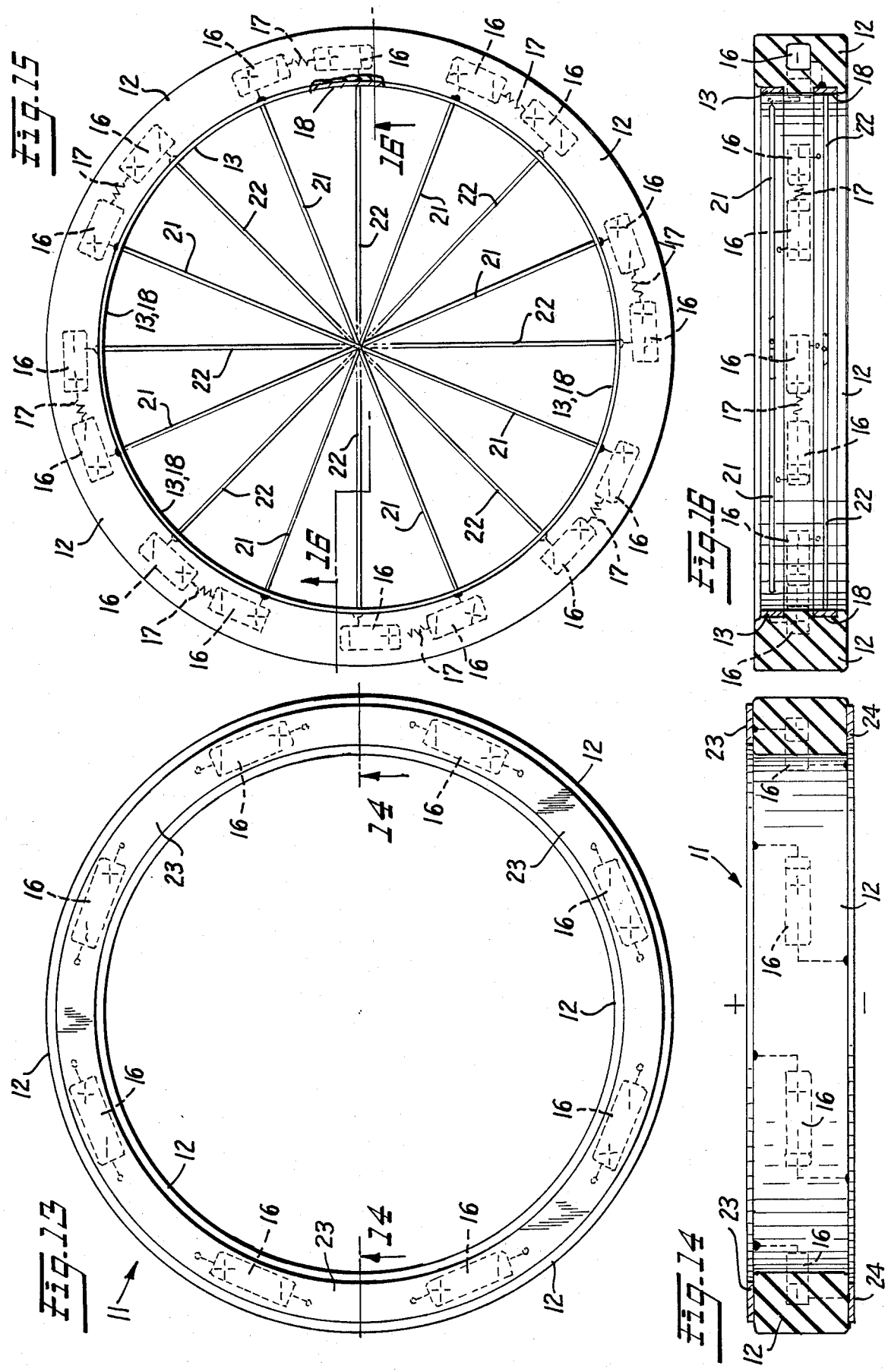

ELECTRIFIED VAGINAL RING

FIELD OF INVENTION

This invention relates to an improved contraceptive device.

More particularly, the invention relates to a new contraceptive device in the form of a vaginal ring which has been electrified.

BACKGROUND OF INVENTION

U.S. Pat. No. 4,616,640 for a "Birth Control Method and Device Employing Electric Forces"—issued Oct. 14, 1986 by Steven Kaali, Peter M. Schwolsky and Joseph W. Porter—inventors, discloses a novel method and device using electric forces within and about the cervical canal of a female human being or other mammal. The electric forces act upon male sperm and prevent migration of the male sperm through the cervical canal and into the uterine cavity where it might fertilize an egg. The present invention is directed to an improved contraceptive device in the form of an electrified vaginal ring which employs the principles of operation disclosed in U.S. Pat. No. 4,616,640.

SUMMARY OF INVENTION

A primary object of the present invention is to provide a novel electrified vaginal ring contraceptive device for use not only as a birth control device, but to kill bacteria, fungus and viruses as well while it is also functioning as a contraceptive.

In practicing the invention, an electrified vaginal ring is provided which comprises an annular ring memoer fabricated from a medical grade plastic, latex or polymeric material which is physically proportioned to fit within the vagina of a female human being or other mammal while surrounding the vaginal wall and/or cervix. The annular ring member has at least two physically spaced-apart electrically conductive surfaces formed thereon from a medical grade conductive material such as platinum or platinum alloy that is biologically compatible with human tissue and fluids. At least one miniaturized electric cell is contained within the annular ring member and has respective ones of its opposite polarity terminals electrically connected to respective ones of the spaced-apart electrically conductive surfaces.

The physically spaced-apart electrically conductive surfaces preferably are in the form of spaced-apart bands of conductive material such as a platinum coated polymer that extends around a major perimeter of the annular ring member and is exposed to human tissue and fluid when inserted in place in the vagina. In the preferred embodiment, a plurality of sub-miniaturized electric cells are formed into miniaturized electric batteries which are embedded within the polymer annular ring member and have their respective positive and negative polarity terminals connected to respective ones of the circular bands of conductive material.

In one particular embodiment of the invention, the spaced-apart bands of conductive material extend around the interior peripheral surface of the annular ring member facing the central opening therein. In a different embodiment, the spaced-apart bands of conductive material extend around the exterior rim-like peripheral surface of the annular ring member. In still another embodiment, the spaced-apart bands of conductive material extend around both the interior peripheral surface of the annular ring member facing the central opening therein and around the exterior rim-like peripheral surface of the annular ring member. In still a different embodiment of the invention, the spaced-apart bands of conductive material are formed on the respective parallel end faces of the annular ring member.

In still a further embodiment of the invention, the annular ring member is a solid electrically insulating medical grade polymer body having a plurality of spaced-apart parallel concentric conductive bands formed on the exposed exterior surface thereof around the interior opening of the annular ring member, and the miniaturized batteries are embedded within the annular body in concentric ring arrays positioned intermediate the concentric, parallel conductive bands and are interconnected with respective opposite polarity terminals thereof being connected to alternate polarity ones of the parallel concentric conductive bands. In a still further embodiment of the invention, the separate spaced-apart bands of electrically conductive material extend only partially around the perimeter of the annular ring member within the central opening so that the partial bands oppose one another in a confronting manner across the opening and are exposed to human tissue and fluids. The miniaturized electric batteries embedded with the annular ring member have their respective positive and negative polarity terminals connected to respective ones of the sets of separate spaced-apart partially encircling bands of electrically conductive material to assure that the electric potentials applied to the sets of confronting opposed bands are of opposite polarity. In a still further embodiment of the invention, conductive wires of platinum, platinum alloys or other suitable conductive material compatible with human tissue are interconnected between different points around the periphery of respective ones of the bands of conductive material circumscribing the central opening in the annular ring member.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference characters, and wherein:

FIG. 1 is a top planar view of one embodiment of the invention;

FIG. 2 is a cross sectional view taken through plane 2—2 of FIG. 1;

FIG. 3 is a top planar view of a second embodiment of the invention;

FIG. 4 is a cross sectional view taken through plane 4—4 of FIG. 3;

FIG. 10 is top planar view of a fifth embodiment of the invention;

FIG. 11 is a cross sectional view taken along lines 11—11 of FIG. 10;

FIG. 12 is a cross sectional view taken along lines 12—12 of FIG. 10;

FIG. 13 is a top planar view of still a further embodiment of the invention;

FIG. 14 is a cross sectional view taken through plane 14—14 of FIG. 13;

FIG. 15 is a top planar view of still another embodiment of the invention which employs cross wires of conductive strips as a part thereof for increasing the intensity of the electric field produced by the device; and FIG. 16 is a cross sectional view taken along lines 16—16 of FIG. 15;

BEST MODE OF PRACTICING THE INVENTION

Figure 7:
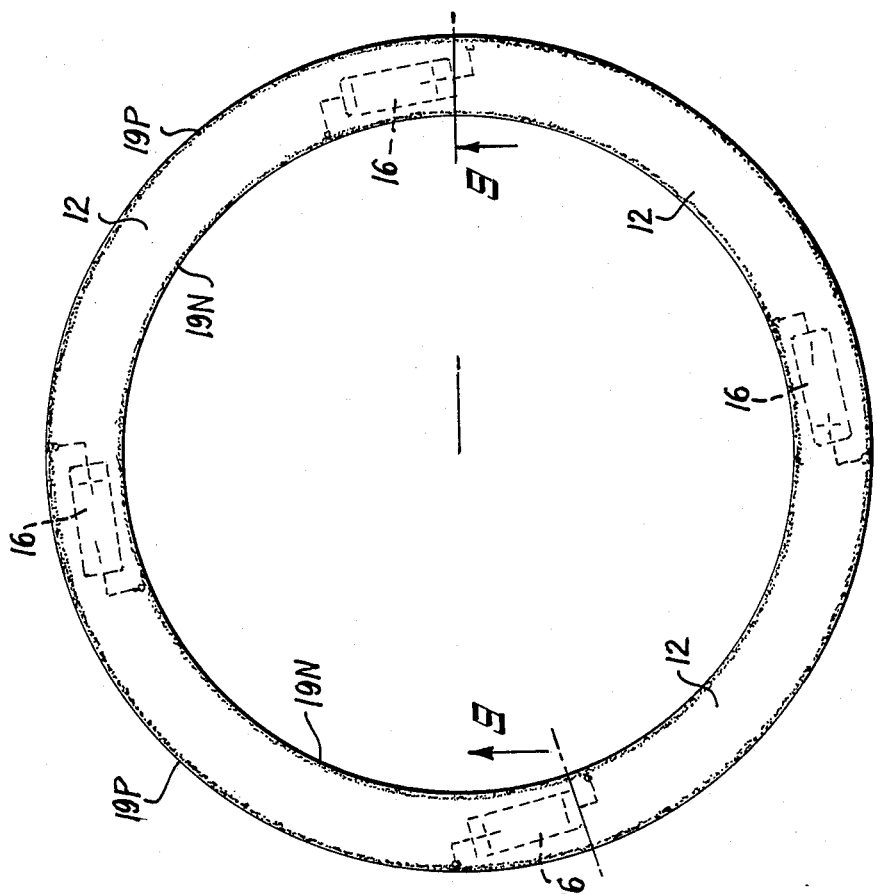
FIG. 7 is a top plan view of a fourth embodiment of the invention.

FIG. 1 is a top plan view of a first embodiment of an electrified vaginal ring constructed in accordance with the present invention. The embodiment of the invention shown in FIG. 1 comprises an annular ring member 12 fabricated from a suitable medical grade plastic material such as a medical grade polymer, latex, silicon or other comparable material that can be readily cast in the form of an annular ring and physically proportioned to fit within the vagina of a female human being or other mammal. The annular ring member 12 is designed to surround the vaginal wall and/or cervix when inserted in the vagina either by the individual wearing the device or by a gynecologist.

FIG. 2 is a cross sectional view of the annular ring member 12 shown in FIG. 1, and best illustrates a pair of physically spaced-apart, electrically conductive surfaces 13 and 18 which are formed so as to circumferentially surround the central opening through the annular ring member 12. The electrically conductive surfaces preferably are in the form of circumferentially surrounding bands which are electrically isolated one from the other and are fabricated from platinum, a platinum alloy or may constitute a platinum or other conductive coating deposited or otherwise formed on the polymer ring member 12 in the manner shown in FIGS. 1 and 2.

When fabricating the annular ring member 12, it has embedded within the body of the ring member a plurality of miniaturized electric batteries 16 which are spaced around the circumference of the annular ring member 12 in the manner shown in FIG. 2. In the embodiment of the invention shown in FIGS. 1 and 2, the batteries 16 are connected with their positive of plus (+) terminals all connected to the upper band-shaped conductive surface 13 and with their negative or minus (−) terminals connected to the conductive band 18. The conductive bands or surfaces 13 and 18 are arrayed around the exposed surface of the central opening through the ring member 12 so that they will be exposed to any fluids within the vagina, such as cervical mucous or semen, as described in the above-referenced U.S. Pat. No. 4,616,640. These surfaces will also be exposed to human flesh and therefore must be fabricated from conductive materials that are compatible with human flesh and fluids.

For a more detailed description of the manner in which the electrified vaginal ring operates, reference is made to the above-noted U.S. Pat. No. 4,616,640, the disclosure of which hereby is incorporated into the disclosure of this application in its entirety. Briefly, however, it can be stated that the electric potential applied between the conductive bands 13 and 18 of the electrified vaginal ring provides an electric field force which is operative within and about the vagina of the female and since the ring in all of its embodiments surround the cervix, the electric field force is particularly concentrated in and about the cervical canal. It is believed that the electric field force acts upon and prevents active male sperm from passing through the cervical canal or even reaching the cervix thereby preventing it from fertilizing a female egg. Accordingly, the device operates as an effective contraceptive.

It is still not clear in what manner the electric field forces prevent male sperm from migrating to and up the cervical canal. One theory is that an induced electric current is caused to flow through the cervical mucous normally discharged during mid-cycle of the female. The electric current flow through this mucous fluid in effect alters the nature of the mid-cycle mucous fluid so that it becomes an effective barrier to the transport of the male sperm. A second theory is that the electric field force which is in the form of an electrostatic field acts upon the active male sperm (known to possess an electrical charge) so as to cause electro-deposition of the sperm onto the electrically conductive electrodes thereby preventing their further passage into and up the cervical canal. A further theory which recently has been developed is that the electrical field within the cervical mucous fluid or semen which function as electrolytes, causes ionization which in turn results in an ion current flow and bombardment of the sperm with ions thereby preventing their further passage into and up the cervical canal. It is also possible that some combination of two or all three of these theories is involved in the effective impediment and prevention of the migration of the male sperm into and up the cervical canal so that the electrified vaginal ring provides an effective contraceptive device.

In addition to its function as a contraceptive, the device also performs an anti-bacterial and/or an anti-fungus and/or an anti-virus function to reduce the possibility of infection in the vagina, the cervix or the uterus by either bacteria, virus or fungus. It is know that male sperm can carry with them either bacteria, virus of fungus of certain types. The electric field forces produced by the electrified vaginal ring induces ion currents while it is being worn that function to scour the bacteria, virus or fungus both directly and by eliminating the male sperm carrier all together, thereby preventing the entrained bacteria, virus or fungus from travelling further into the vagina or into and up the cervix or the uterus.

Lastly, it should be noted that the semen of a male human or male mammal can and does function as an electrolyte both during operation and to initiate operation of the electrified vaginal ring so that it functions as an effective contraceptive. Thus, the presence of such fluids can be used to initiate activation of the electrified vaginal ring in a manner such that the occurrence of semen in the vagina and around the cervix with the electrified vaginal ring in place, can serve to activate the device and prevent sperm from progressing further through the vagina or into and up the cervical canal to the uterine cavity.

FIGS. 3 and 4 of the drawings illustrate a second embodiment of the invention which is quite similar to that shown in FIGS. 1 and 2 with the exception that the electrically conductive surfaces formed on the annular ring member 12 are provided as bands 14 and 15 which circumscribe the exterior periphery of the annular ring member 12. In this embodiment the internally embedded miniaturized batteries 16 have their plus terminals (+) connected to the upper band 14 and their negative terminals (−) connected to the lower conductive band 15. This embodiment of the electrified vaginal ring in operation would extend its electric field forces a little more widely within the vagina than would be true of the embodiment shown in FIGS. 1 and 2, which tends to concentrate its field force around the central opening surrounding the cervix while being worn.

Figure 5:
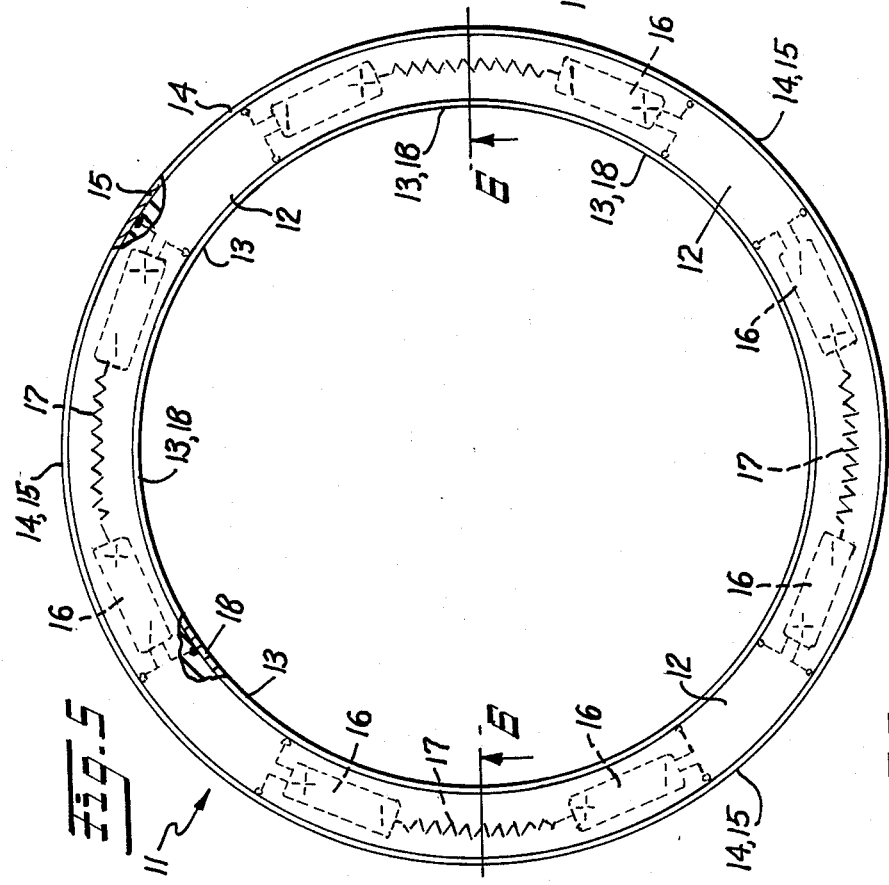
FIG. 5 is a top planar view of a third embodiment of the invention.
Figure 6:
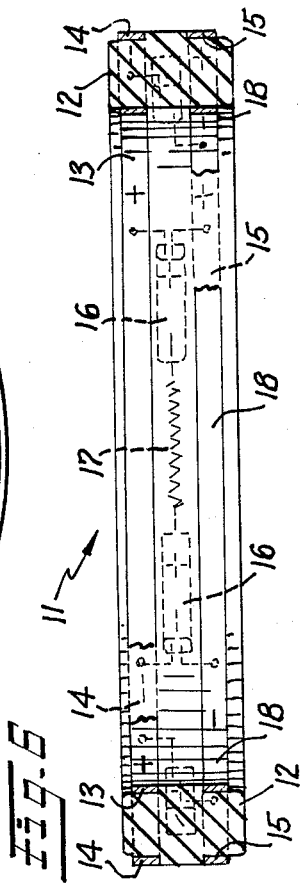
FIG. 6 is a cross sectional view taken through plane 6—6 of FIG. 5.

In order to combine the best features of both the embodiment shown in FIGS. 1 and 2 and the embodiment shown in FIGS. 3 and 4, the species of the invention shown in FIGS. 5 and 6 is provided. The electrically conductive surfaces provided in the electrified vaginal ring shown in FIGS. 5 and 6, are formed by two internal circumferentially extending bands 13 and 18 in FIGS. 1 and 2 and also in two externally circumferentially surrounding bands 14 and 15 similar to FIGS. 3 and 4. With this arrangement, both the concentration of the electric field forces over the central opening (and hence over the cervix) while the device is being worn, is obtained along with the more widespread distribution of the electric field forces by reason of the provision of the external circumferentially extending bands 14 and 15.

In addition to the above, it should be noted that adjacent bands 14 and 13 on the upper side of the annular ring member 12 shown in FIGS. 5 and 6 are provided with opposite polarity excitation potentials as are the adjacent bands 15 and 18 on the lower end of the vaginal ring member 12. As a consequence, electric field lines of force will extend not only between bands 13 and 18 within the internal opening through the center of the annular ring member 12 and between the bands 15 and 14 exteriorly of the annular ring member; but, also electric lines of force will extend between the positive ring member 13 on the inside of the annular ring member and the negative polarity ring member 14 on its upper exterior side. Similarly, electric lines of force will extend between conductive bands 15 and 18 on the lower end of the annular ring member so that in effect electric lines of force extend completely around the cross section of the annular ring member 12. This results in increasing substantially the space within the vagina subjected to the action of the electric field forces.

In order to provide a selected and adequate value electric potential for application to the respective electrodes 13, 14, 15 and 18, the miniaturized batteries 16 are connected in series circuit relationship to form an increased capacity battery pack system. The batteries 16 are interconnected in the manner shown in FIGS. 5 and 6 through respective current limiting resistors fabricated in microcircuit form and which are tailored to provide a desired voltage and current acting for the serially connected battery system.

Figure 8:
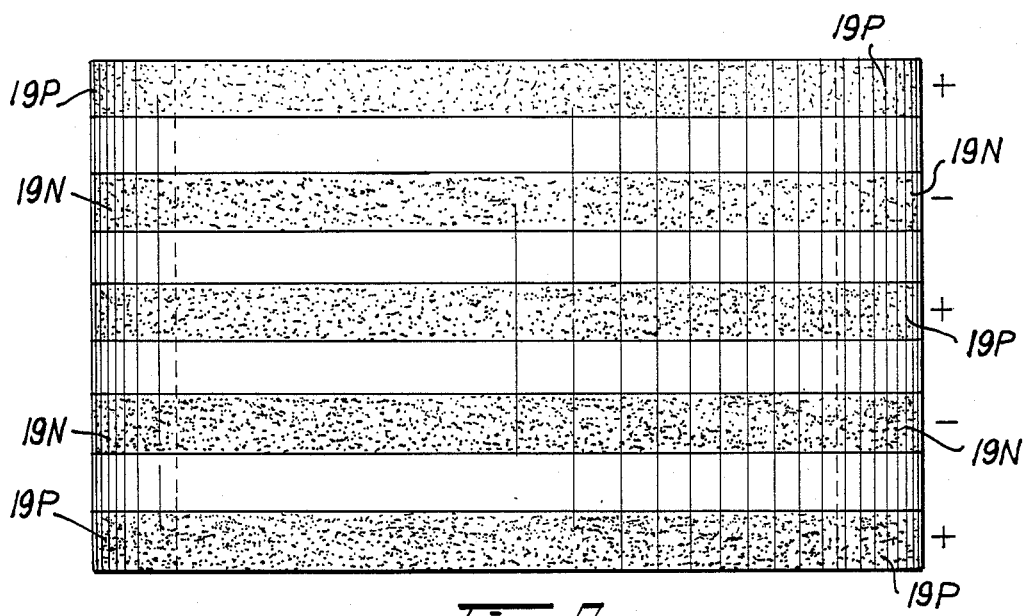
FIG. 8 is a side view of the electrified vaginal ring shown in FIG. 7.
Figure 9:
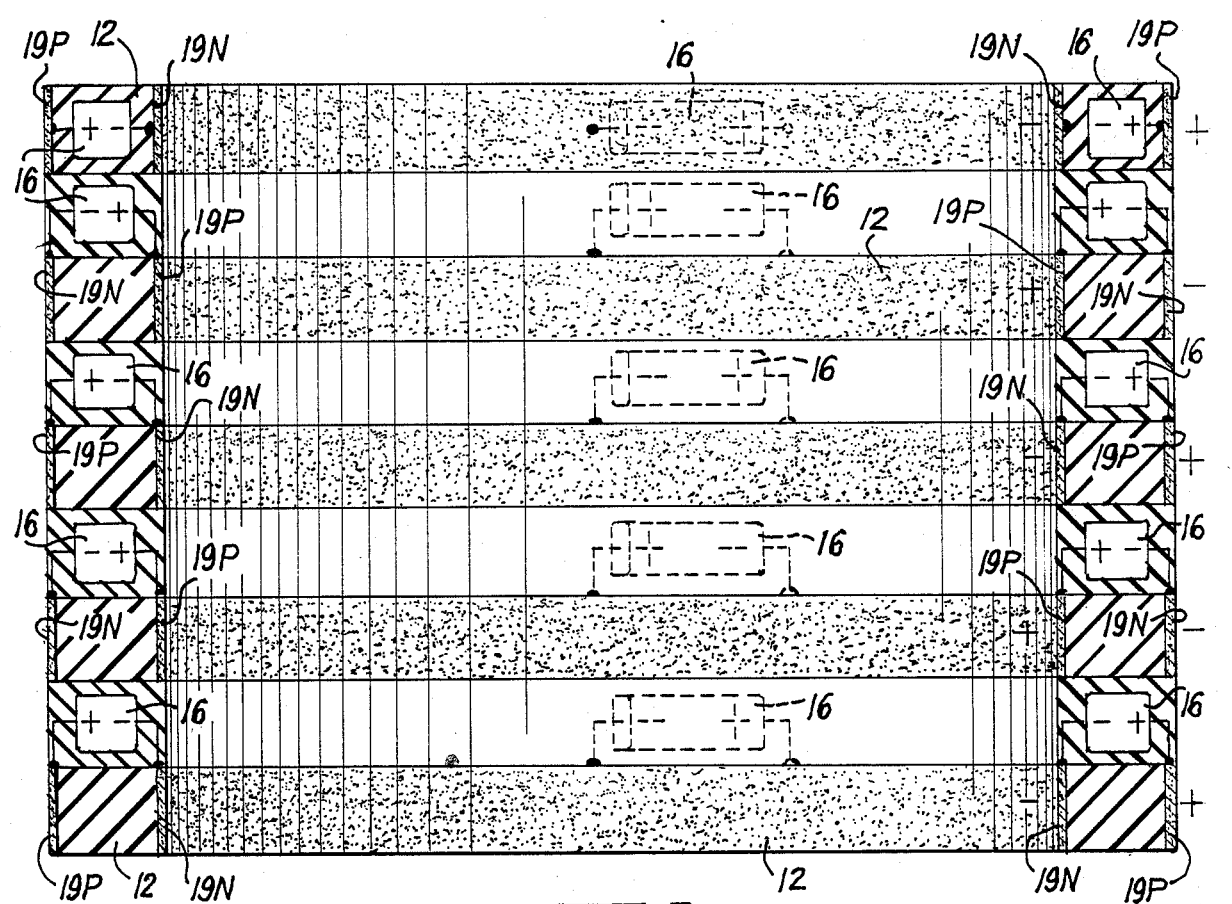
FIG. 9 is a longitudinal sectional view taken through plane 9—9 of FIG. 7.

FIGS. 7, 8 and 9 illustrate a somewhat different form of the electrified vaginal ring which employs a more elongated annular ring member 12 fabricated from a suitable medical grade polymer, and elastomer such as latex or a silicon body member on which a plurality of spaced-apart, parallel, concentric electrically conductive bands 19P and 19N are formed. In this embodiment of the invention preferably five such bands are formed both around the exterior periphery of the body member 12 as well as around the surface of the central opening through the annular body member 12. Miniaturized batteries 16 are embedded within the annular body member 12 in concentric ring arrays positioned intermediate the concentric parallel conductive bands 19P and 19N. The miniaturized batteries 16 are connected as best shown in FIG. 9 with their negative terminals connected to respective ones of the conductive bands 19N and their positive terminals connected to respective ones of the positive polarity conductive bands 19P. It should also be noted that adjacent bands of conductive material around the outside periphery and around the exposed surface of the central opening through annular member 12 are of opposite polarity so that electric field lines of force will extend around both ends of the annular ring member 12 as well as along the outside and between the parallel concentric conductive bands extending internally through the ring member in the manner similar to that described with relation to the electrified vaginal ring shown in FIGS. 5 and 6 of the drawings. If desired, a set of concentric, track-like conductive bands could be formed around both the top and bottom ends of the elongated annular ring member shown in FIGS. 7, 8 and 9 in a manner similar to that to be described with relation to FIGS. 13 and 14 of the drawings (to be described more fully hereafter) in order to further enhance the field strength of the electric lines of force extending around the ends of the annular ring body member 12 shown in FIGS. 7, 8 and 9.

FIGS. 10, 11 and 12 of the drawings illustrate still a different embodiment of the invention in which the electrically conductive surfaces 13 and 18 are formed so as to constitute half arcs or semicircles around the central inner opening through the center of the annular ring member 12. For this purpose, the annular ring member 12 has a set of diametrically opposed, integral, integrating segments 12I formed on its internal surface so as electrically insulate and isolate the semicircular electrically conductive band halves 13 and 18 on one side of the annular ring member from the semicircular set of band halves 13 and 18 formed on the opposite side. The miniaturized batteries embedded in the ring member 12 on one side then are connected with their positive terminals (+) connected to the semicircular conductive band 13 halves and their negative terminals (−) connected to the semicircular conductive band halves 18 as best shown in FIG. 11 of the drawings. In contrast, on the opposite side of the annular ring member 12, the miniaturized batteries 16 have their negative terminals (−) connected to the semicircular conductive band halves 13 and their positive terminals (+) connected to the semicircular conductive band halves 18 as shown in FIG. 12 of the drawings.

With this arrangement, the electric field lines produced between the diametrically opposed, semicircular conductive band halves 13 will extend across the central opening through the annular ring member 12 and a similar effect will be obtained between the two opposite polarity semicircular conductive band halves 18 so that in effect the dual stage electric field is produced and extends across the central opening to the annular ring member 12. If desired, conductive bands such as shown at 14 and 15 in FIGS. 3 and 4 or as shown at 23 and 24 in FIGS. 13 and 14 could be provided to the species of the invention shown in FIGS. 10, 11 and 12.

FIGS. 13 and 14 illustrate still a further embodiment of the invention which again employs an annular ring member 12 formed of a medical grade polymer, elastomer, silicone or other suitable plastic material which is compatible with human tissue and fluids and which includes a plurality of miniature-sized batteries 16 molded within the body or rim portion of the annular ring member 12. At least two physically spaced-apart electric conductive surfaces are formed on the opposite, parallel end surfaces of annular ring body member 12 which are in the form of flat, race track-type conductive bands 23 and 24 electro-deposited, sprayed or otherwise formed on the opposite parallel top and bottom surfaces of annular ring body member 12 as best shown in FIGS. 14 and 15. The respective race track-type electrically conductive bands 23 and 24 are supplied with opposite polarity electric potential from the respective opposite polarity terminals plus and minus of the individual batteries 16 molded within body member 12 as best seen in FIGS. 15.

In operation, the electric field forces produced by the potential difference existing between conductive bands 23 and 24 will extend between the two bands 23 and 24 both through the central opening in the annular ring body member 12 and around the outside exterior surfaces so as to provide both a concentrated internal electric force field and a widely displaced electric force field for maximizing the effect of the electrical force on male sperm entering the vagina and preventing the sperm from reaching the cervix, the cervical canal and the uterus.

FIGS. 15 and 16 illustrate an embodiment of the electrified vaginal ring which is substantially identical in construction to the first embodiment shown in FIGS. 1 and 2, but differs therefrom in that it includes a set of at least two, but preferably more, conductive wires which are connected across diametrically opposite points from the respective conductive bands 13 and 18. As shown in FIGS. 15 and 16, there is a set of six conductive wires 21 connected between diametrically opposite points on the upper conductive rim or band 13 formed around the open inside surface of the annular ring member 12. These conductive wires 21 preferably all are joined at a central point and are maintained at the same positive potential developed by the respective miniaturized batteries 16 molded within the body of the annular ring member 12. In a similar fashion, diametrically opposite points on the lower conductive band 18 are interconnected by conductive wires 22 which also are joined at their center crossing point and maintained at the same negative potential as that of the miniaturized batteries 16. The conductive wires 21 and 22 all may be formed of platinum or a platinum alloy or polymers or other similar, relatively strong conductive materials that is compatible with human tissue and body fluids. It should be noted that because electrically conductive bands 13 and 18 are displaced apart one over the other, the sets of interconnecting wires 21 and 22 will cross in different horizontally extending planes which are vertically displaced apart by the same distance as the spacing between the conductive bands 13 and 18.

The existence of the different polarity electric potential on each of these sets of cross wires results in the production of an intense electric field in the space between the wires which is quite uniform and can be adjusted by proportioning the size and capacity of the miniature battery system 16 to assure complete screening and electric force treatment of any male sperm attempting to pass through the central opening of the electrified vaginal ring. The miniaturized battery system connected to the respective bands 13 and 18 and across the respective sets of cross wires 21, 22 operate in substantially the same manner as in the miniaturized battery systems 16, 17 described more fully above with relation to FIGS. 5 and 6 of the drawings. As a result, the value of the excitation potential developed by the battery system 16, 17 across the sets of cross wires 21, 22 can be precisely tailored to a desired value for optimum operation of the electrified vaginal ring both as a contraceptive device and for scouring of bacteria fungus and viruses.

INDIVIDUAL AND COMMERCIAL APPLICABILITY

From the foregoing description, it will be appreciated that the invention provides a novel electrified vaginal ring device for use not only as a contraceptive in the practive of birth control measures, but also can be used as an anti-bacteria, anti-fungus and anti-virus control device for killing bacteria, fungus and viruses that might be introduced into the vagina of a female human being or other female mammal due to semen or other body fluids.

Having described several embodiments of a novel electrified vaginal ring constructed in accordance with the invention, it is believed obvious that other modifications and variations of the invention will be suggested to those skilled in the art in the light of the above teachings. It is therefore to be understood that changes may be made in the particular embodiments of the invention disclosed which are within the full intended scope of the invention as defined by the appended claims.

What is claimed is:

1. An electrified vaginal ring comprising an annular ring member of a medical grade plastic physically proportioned to fit within the vagina of a female human being or other mammal while internal circumscribing the vaginal wall and/or surrounding the cervix, said annular ring member having at least two physically spaced-apart electrically conductive surfaces electrically insulated from each other formed thereon from a medical grade conductive material that are exposed to and compatible with human tissue and fluids, and at least one miniaturized self-contained, electric cell embedded within the annular ring member and having respective ones of its opposite polarity terminals electrically connected to respective ones of the spaced-apart electrically conductive surfaces.

2. An electrified vaginal ring according to claim 1 wherein the physically spaced-apart electrically conductive surfaces are in the form of spaced-apart bands of conductive material extending around a major perimeter of the annular ring member and exposed to human tissue and fluids, and wherein there are a plurality of electric cells formed into self-contained miniaturized electric batteries embedded within the annular ring member and having respective positive and negative polarity terminals connected to respective different ones of the circular bands of conductive material.

3. An electrified vaginal ring according to claim 2 wherein the spaced-apart bands of conductive material extend around the interior peripheral surface of the annular ring member facing the central opening therein.

4. An electrified vaginal ring according to claim 2 wherein the spaced-apart bands of conductive material extend around the exterior rim-like peripheral surface of the annular ring member.

5. An electrified vaginal ring according to claim 2 wherein the spaced-apart bands of conductive material extend around both the interior peripheral surface of the annular ring member facing the central opening therein and around the exterior rim-like peripheral surface of the annular ring member.

6. An electrified vaginal ring according to claim 5 wherein adjacent spaced-apart bands of conductive material are maintained at opposite polarity electric potentials.

7. An electrified vaginal ring according to claim 2 wherein the spaced-apart bands of conductive material are formed on the respective parallel end faces of the annular ring member.

8. An electrified vaginal ring according to claim 2 wherein the annular ring member is a solid electrically insulating annular body having a plurality of spaced-apart parallel concentric conductive bands formed on an exposed surface thereof with the miniaturized batteries being embedded within the annular body in concentric ring arrays positioned intermediate the concentric parallel conductive bands and being interconnected with the respective opposite polarity terminals thereof being connected to alternate polarity ones of parallel concentric conductive bands.

9. An electrified vaginal ring according to claim 8 wherein the plurality of spaced-apart parallel concentric conductive rings are formed both around the exterior periphery and around the interior opening of the annular body of the annular ring member.

10. An electrified vaginal ring according to claim 1 wherein the physically spaced-apart electrically conductive surfaces are in the form of separate spaced-apart bands of electrically conductive material which extend partially around the perimeter on opposite sides of the central opening in the annular ring member so as to oppose one another in confronting relationship across the opening and are exposed to human tissue and fluids, and wherein there are a plurality of electric cells formed into miniaturized electric batteries embedded within the annular ring member and having respective positive and negative polarity terminals connected to respective ones of the separate spaced-apart bands of electrically conductive material to assure that the electric potentials applied to sets of confronting opposed bands of electrically conductive material are of opposite polarity.

11. An electrified vaginal ring according to claim 2 wherein between different points around the periphery of the respective ones of the bands of conductive material circumscribing the central opening in the annular ring member at least two electrically conductive cross wires or strips are connected, said cross wire or strip being at opposite electric polarity potentials and formed of a material that is compatible with human flesh and fluids.

12. An electrified vaginal ring according to claim 11 wherein there are a plurality of pairs of electrically conductive cross wires or strips of opposite electric polarity connected across the central opening through the annular ring member.

* * * * *